(12) United States Patent
Neuss et al.

(10) Patent No.: US 8,545,824 B2
(45) Date of Patent: *Oct. 1, 2013

(54) GLYCEROL ETHER MIXTURE, COSMETIC COMPOSITION CONTAINING THIS MIXTURE AND PROCESS FOR ITS PRODUCTION

(75) Inventors: Michael Neuss, Koelnq (DE); Thomas Albers, Duesseldorf (DE); Stefan Bruening, Philadelphia, PA (US); Achim Ansmann, Erkrath (DE); Helga Gondek, Duesseldorf (DE); Karl Heinz Schmid, Mettmann (DE)

(73) Assignee: Cognis IP Management GmbH, Duesseldorf (DE)

( * ) Notice: Subject to any disclaimer, the term of this patent is extended or adjusted under 35 U.S.C. 154(b) by 30 days.

This patent is subject to a terminal disclaimer.

(21) Appl. No.: 12/822,671

(22) Filed: Jun. 24, 2010

(65) Prior Publication Data
US 2010/0261798 A1    Oct. 14, 2010

Related U.S. Application Data

(63) Continuation of application No. 11/121,392, filed on May 4, 2005, now Pat. No. 7,776,317.

(51) Int. Cl.
*A61K 8/86* (2006.01)
*A61K 8/00* (2006.01)
*A61K 8/72* (2006.01)
*A61K 8/02* (2006.01)

(52) U.S. Cl.
USPC .............................................. 424/65; 514/772

(58) Field of Classification Search
USPC .......................................... 424/65; 514/772
See application file for complete search history.

(56) References Cited

U.S. PATENT DOCUMENTS 5,516,510 A * 5/1996 Beilfuss et al. ................. 424/65
2004/0254404 A1 * 12/2004 Albers et al. ................... 568/679

FOREIGN PATENT DOCUMENTS

WO    WO03055559    *   8/2003

\* cited by examiner

*Primary Examiner* — Janet Epps-Smith
*Assistant Examiner* — Courtney Brown
(74) *Attorney, Agent, or Firm* — Servilla Whitney LLC

(57) ABSTRACT

The invention relates to a glycerol ether mixture which consists essentially of a) at least one $C_{12-22}$ glycerol monoalkyl ether, b) at least one $C_{12-22}$ glycerol dialkylether and optionally c) at least one $C_{12-22}$ glycerol trialkyl ether and/or d) at least one $C_{12-22}$ fatty alcohol, components a) and b) together making up at least 50% by weight of the glycerol ether mixture and the ratio by weight of component a) to component b) being in the range from 3:1 to 1:2. The invention also relates to a process for producing the glycerol ether mixture and to cosmetic compositions containing the glycerol ether mixture.

9 Claims, No Drawings

GLYCEROL ETHER MIXTURE, COSMETIC COMPOSITION CONTAINING THIS MIXTURE AND PROCESS FOR ITS PRODUCTION

RELATED APPLICATIONS

This application is a continuation of U.S. application Ser. No. 11/121,392, filed May 4, 2005 which claims priority from German Application No. 10 2004 022 252.5 filed May 4, 2004, the entire contents of which are incorporated by reference.

BACKGROUND OF THE INVENTION

The use of glycerol monoalkyl ethers in cosmetic compositions is already known in principle. Thus, EP 0 599 433 A1 describes glycerol monoalkylethers containing a $C_{6-18}$ and preferably a $C_{6-12}$ alkyl group as a deodorizing component in aqueous or alcoholic deodorant solutions. In DE 100 47 759 A1, $C_{6-18}$ glycerol monoalkyl ethers are used as antimicrobial components in wet wipes. In this case, too, the shorter chain glycerol monoalkyl ethers are preferred.

By virtue of their ether structure, partial glycerol ethers are stable to hydrolytic or catalytic degradation reaction by acidic antiperspirant salts (aluminium or aluminium/zirconium salts) which is a very important criterion for their use as raw materials in the antiperspirant field.

Hitherto, glycerol ethers have acquired little significance as emulsifiers or consistency factors for cosmetic compositions. In water-containing antiperspirant/deodorant emulsions, fatty alcohols, such as cetearyl, stearyl and behenyl alcohol, fatty acid esters and also triglycerides, such as glycerol monostearate, are normally used as co-emulsifiers or as consistency factors. By virtue of their chemical structure, fatty alcohols and hydroxyfatty acids are stable whereas fatty acid esters and triglycerides, such as glycerol monostearate, are not.

The performance-related development of stable and viscosity-stable, but sensorially agreeable emulsions is a major challenge to the developer, particularly in the antiperspirant/deodorant field. The high salt content, the low pH and the fact that the antiperspirant components dissolved in water give rise to distinctly tacky end properties in the formulation call for new raw material solutions in the field of antiperspirant/deodorant waxes in order to develop improved antiperspirant/deodorant formulations.

Fatty alcohols, such as cetearyl, stearyl and behenyl alcohol, and hydroxyfatty acids, such as 12-hydroxystearic acid, in combination with the polymeric N-acrylic acid amide are frequently used in water-free antiperspirant stick and soft solid formulations (cf. U.S. Pat. No. 5,429,816 A). Systems such as these do not always leave an optimal feeling on the skin after application, even when optimized emollients are used.

Accordingly, the problem addressed by the present invention was to provide an emulsifier or consistency factor which would be suitable for use over a broad range of applications and which, in the field of aqueous o/w emulsions or solid cosmetic compositions and particularly in antiperspirant/deodorant formulations, would lead to stable products with agreeable sensory properties.

BRIEF SUMMARY OF THE INVENTION

As a solution to the problems stated above, this invention provides a novel glycerol ether mixture having advantageous emulsifier and consistency-imparting properties for cosmetic compositions including it, particularly antiperspirant compositions.

Accordingly, in a first embodiment, the present invention relates to a glycerol ether mixture which consists essentially of a) at least one $C_{12-22}$ glycerol monoalkyl ether,
b) at least one $C_{12-22}$ glycerol dialkylether and optionally
c) at least one $C_{12-22}$ glycerol trialkyl ether and/or
d) at least one $C_{12-22}$ fatty alcohol, components a) and b) together making up at least 50% by weight of the glycerol ether mixture and the ratio by weight of component a) to component b) being in the range from 3:1 to 1:2.

DETAILED DESCRIPTION OF THE INVENTION

It has now surprisingly been found that a mixture consisting at least of mono- and dialkyl ethers of glycerol in the particular ratio by weight mentioned above has extremely good emulsifying and consistency-imparting properties. These properties are superior to those of the mono- or dialkyl ethers of glycerol used on their own. Particularly advantageous properties are obtained when the ratio by weight of component a) ($C_{12-22}$ glycerol monoalkyl ether) to component b) ($C_{12-22}$ glycerol dialkyl ether) is in the range from 1:1 to 1.3.1.

The glycerol ether composition according to the invention may consist solely of components a) and b) mixed in the ratio mentioned above. However, $C_{12-22}$ glycerol trialkyl ethers (component c)) and/or $C_{12-22}$ fatty alcohol (component d)) may also be present in the mixture—generally from the production process. However, the predominant part of the glycerol ether mixture consists of components a) and b) which, together, make up at least 50% by weight, more particularly more than 60% by weight and, in a particularly preferred embodiment, more than 70% by weight of the mixture. Besides components a) to d), small amounts of other components may be present in the composition. These other components may also enter the mixture, for example, through the production process. Typical accompanying substances are, for example, water residues and impurities emanating from the raw materials used. Their percentage content in the claimed glycerol ether mixture is at most 10% by weight and preferably at most 5% by weight. Accordingly, the words "consists essentially of" in the context of the invention mean that at least 90% by weight of the claimed glycerol ether mixture consists of components a) and b) and—where present—components c) and/or d).

The $C_{12-22}$ alkyl group of components a) to d) may be a saturated or unsaturated, branched or unbranched alkyl group. Suitable groups are, for example, cetyl, palmitoleyl, stearyl, isostearyl, oleyl, elaidyl, petroselinyl, linolyl, linolenyl, elaeostearyl, arachyl, gadoleyl, behenyl, erucyl and brassidyl. Technical mixture thereof, as obtained for example from natural fats and oils, may also be present.

$C_{16-18}$ alkyl groups, particularly saturated and unbranched types, are particularly preferred.

Basically, each of the individual components of the glycerol ether mixture according to the invention may be separately prepared and then mixed together in a suitable ratio. In such cases, the alkyl groups of the individual components may differ from one another. In a preferred embodiment, however, alkyl is the same for all components a) to d). Production is then preferably carried out so that the mixture of components a) and b) and optionally c) and d) is directly obtained from the reaction in the desired concentration distribution.

A particularly suitable (co)emulsifier or consistency factor in cosmetic compositions is a glycerol ether mixture which consists essentially of 35 to 45% by weight of component a), 25 to 45% by weight of component b), 1 to 5% by weight of component c) and 8 to 27% by weight of component d). Even more preferred is a glycerol ether mixture which consists essentially of 40% by weight of component a), 30 to 40% by weight of component b), 2 to 3% by weight of component c) and 13 to 22% by weight of component d).

As already mentioned, the glycerol ether mixture according to the invention is preferably produced so that the mixture of the individual components in the desired quantities is obtained as the reaction product of the synthesis. A modification of the process described in applicants' WO 03/040072 A1 is particularly suitable. Here, the synthesis is mainly directed towards the formation of monoalkyl ethers, the dialkyl ethers generally being formed in quantities of no more than 10% by weight and at most 16% by weight. In order to bring the ratio of mono- to dialkyl ethers into the range required in accordance with the invention and to increase the percentage of more highly etherified products, the percentage of glycerol in the educts is reduced by comparison with the Examples described in WO 03/040072 A1.

Accordingly, in the process according to the invention for the production of the glycerol ether mixture, as in the process according to WO 03/040072 A1, glycerol is deprotonated with a base and the water formed is continuously removed from the reaction mixture, the deprotonated glycerol is reacted with a component Z) selected from an alkyl sulfate or a sulfuric acid alkyl ester and the solid phase formed and the aqueous phase are separated from the glycerol ether mixture formed. In contrast to WO 03/040072 A1, however, the glycerol is used in a molar ratio of 4:1 to 2:1 to component Z). A ratio of glycerol to component Z) of about 3:1 is particularly suitable for obtaining the particularly preferred glycerol ether mixtures according to the invention.

For all other process parameters, working up and purification steps, etc., reference may be made to WO 03/040072 A1.

In another embodiment, the present invention relates to a cosmetic composition which contains the glycerol ether mixture according to the invention as an emulsifier and/or consistency factor.

The nature of the cosmetic composition is not particularly limited. The glycerol ethers present in the mixture according to the invention are solid, wax-like compounds. Accordingly, the glycerol ether mixture may be incorporated in any cosmetic compositions which, hitherto, already contained waxes, above all waxes with emulsifying or consistency-imparting properties. Accordingly, suitable cosmetic compositions range from water-free solid formulations, for example stick formulations (deodorant sticks, lipsticks, etc.) and semisolid formulations (so-called soft solids as used inter alia in deodorant preparations) to aqueous emulsions (o/w emulsions for creams, lotions, roll-on deodorants, etc.).

The glycerol ether mixture according to the invention is particularly suitable as an emulsifier or consistency factor in cosmetic compositions. The components otherwise present in the cosmetic compositions, such as emollients (oil components, fats, waxes), cosmetic or pharmaceutical active principles, thickeners, superfatting agents, fillers, dyes, pigments, stabilizers (antioxidants, preservatives), UV filters, film formers, swelling agents, hydrotropes and perfume oils, may basically be used as before. Accordingly, they need not be discussed any further herein.

Particularly favorable results are obtained when the glycerol ether mixture makes up from 0.2 to 20% by weight and more particularly 0.5 to 5% by weight of the cosmetic composition.

Whereas, basically, the glycerol ether mixture may be used as sole emulsifier or consistency factor, a preferred cosmetic composition contains the glycerol ether mixture in combination with at least one other emulsifier and/or consistency factor. In this case, the quantity of the glycerol ether mixture depends on the other components used. Basically, however, the glycerol ether mixture makes up from 5 to 90% by weight, more particularly from 10 to 80% by weight and preferably from 15 to 75% by weight of the total quantity of all emulsifiers.

Particularly good consistency-imparting properties for the cosmetic composition are achieved when the glycerol ether mixture according to the invention is used in admixture with triglycerides, such as hydrogenated castor oil, with fatty alcohols, such as stearyl alcohol or behenyl alcohol, or with hydroxyfatty acids, such as 12-hydroxystearic acid. The $C_{16-22}$ partial glycerol ethers in particular have a strong consistency-imparting influence on various emollients and, accordingly, are most particularly suitable for water-free antiperspirant soft solid and stick formulations.

Over and above the pure consistency-imparting properties, extremely homogeneous inner structures and surface structures are obtained in the cosmetic formulation with the glycerol ether mixtures according to the invention. With the high sensory demands antiperspirant products are being increasingly expected to satisfy by consumers in mind, the new glycerol ether mixture has a greatly improved influence on the overall sensory impression of the water-free final formulation. Thus, greater skin smoothness and softness are obtained which leads to a distinctly increased skin-care impression of the formulation as a whole.

Even in water-based antiperspirant/deodorant emulsions, these waxes show very favorable consistency-imparting properties through the build-up of lamellar phases which have proved to be extremely stable. Besides improved emulsion stabilities, increased viscosity stability in storage is also obtained. By virtue of the chemical structure of these partial glycerides and the lamellar structure ensuing therefrom, an extremely caring, but also light overall sensory impression of the formulations on the skin of the user is obtained. The partial glycerides also show very good (co)emulsifying properties in PIT emulsions and thus provide very stable, thinly liquid emulsions.

Accordingly, a preferred application of the invention is in the field of antiperspirant formulations. A particularly preferred cosmetic composition is distinguished by the fact that it contains at least one deodorizing, astringent or antimicrobial compound.

The invention is illustrated by the following Examples.

EXAMPLES

Example 1

Production of a Glycerol Ether Mixture According to the Invention

In a 2-liter four-necked flask, 276 g (3 mol) glycerol were heated to 120° C., 100 g (1.25 mol) 50% sodium hydroxide were slowly added dropwise and the water formed was continuously removed by condensation at 120° C. under a vacuum of 100 mbar. Towards the end of the removal of water, the vacuum was reduced to 10 mbar. 380 g (1 mol) Lanette E powder (sodium cetyl stearyl sulfate powder) were added to and suspended in the Na gycerolate thus formed and the resulting suspension was stirred for 8 h at 180° C. The reaction was monitored by determining the anionic surfactant content which, after a reaction time of 8 hours, was well below 1%. For working up, the reaction mixture was mixed with 225 ml water and 5 ml 50% sodium hydroxide at a temperature of 90° C. and the mixture was then left standing for phase separation. The phases formed were then separated. To this end, the lower phase was filtered to remove the sodium sulfate precipitated and the upper organic phase (glycerol ether phase) was washed with 250 ml water at a temperature of 90° C. The phases were separated again. The organic phase was freed from water by vacuum distillation. The $C_{16/18}$ glycerol ether mixture remained in the distillation residue. The product contained ca. 40% by weight mono-$C_{16/18}$-glycerol ether, ca. 40% by weight di-$C_{16/18}$-glycerol ether, ca. 2% by weight tri-$C_{16/18}$-glycerol ether and ca. 15% by weight $C_{16/18}$ fatty alcohol.

Comparison Example 1

Preparation of a Glycerol Ether Mixture for Comparison Purposes

A glycerol ether mixture containing glycerol monoether and diether in a ratio of 1:4 was prepared as in Example using 0.5 mol instead of 3 mol glycerol.

Formulation Examples

Production of Cosmetic Compositions

Various cosmetic compositions were prepared using the glycerol ether mixture prepared in Example 1. Comparison formulations were additionally prepared with the glycerol ether mixture of Comparison Example 1, the corresponding monoglycerol ether and other typical emulsifiers or consistency factors.

The compositions of the cosmetic preparations are shown in Tables 1 to 5 below. Table 1 contains formulation examples for antiperspirant creams and roll-ons, Table 2 contains formulation examples for skin-care creams, Table 3 contains formulations for lipsticks, Table 4 contains formulation examples for sun creams and body and face care creams and, finally, Table 5 contains formulation examples for antiperspirant sticks and soft solids. The quantities in which the components are used are shown in % by weight. In the Tables, the Comparison Examples are denoted "C . . . " and the Examples according to the invention are denoted "E . . . ".

Some of the formulations were tested for their properties.

The viscosity measurements were carried out with a Brookfield RVF viscosimeter (spindle 5, 10 r.p.m.) for the formulations of Table 1 and with a Brookfield RVT viscosimeter (spindle TE, 4 r.p.m. with Helipath) for the formulations of Table 2. The hardness measurements were carried out with a Petrotest PNR 10 penetrometer from Petrotest Instruments GmbH & Co. KG (microcone: 5.0 g; drop bar: 47.5 g; measuring temperature: 23° C.; hardness=mm depth of penetration in 5 seconds).

The sensory tests were carried out by 4 trained testers. To this end, the formulations were applied to the forearm of the test person and the following criteria were evaluated on a scale of −2 to +2: structure (−2: very inhomogeneous to +2: very homogeneous), viscosity stability and stability (−2: poor to +2: high), sensory impression (−2: poor to +2: very good) and oil secretion (−2: serious to +2: none). The results are set out in the following Table as averages of the individual evaluations.

TABLE 1

| | | Antiperspirant creams and roll-ons | | | | | | | |
|---|---|---|---|---|---|---|---|---|---|
| Constituents | INCI | C1 | C2 | C3 | C4 | C5 | C6 | C7 | C8 |
| Eumulgin B2 | Ceteareth-20 | 2.0 | 2.0 | 2.0 | 2.0 | 2.0 | 2.0 | 2.0 | 2.0 |
| Eumulgin B3 | Ceteareth-30 | — | — | — | — | — | — | — | — |
| Eumulgin S2 | Steareth-2 | — | — | — | — | — | — | — | — |
| Lanette O | Cetearyl Alcohol | 5.0 | 5.0 | — | — | — | — | — | — |
| Lanette 22 | Behenyl Alcohol | — | — | — | — | — | — | — | — |
| Cutina MD | Glycerylstearate | — | — | 5.0 | 5.0 | — | — | — | — |
| C16/18-Monoglycerol ether | | | | | | 5.0 | 5.0 | | |
| Glycerol ether mixture, Comp. Ex. 1, mono/di (1:4) | | | | | | | | 5.0 | 5.0 |
| Glycerol ether mixture, Ex. 1, mono/di (1:1) | | — | — | — | — | | | | |
| Cetiol S | Diethylhexyl-cyclohexane | 16.0 | — | 16.0 | — | 16.0 | — | 16.0 | — |
| Eutanol G16S | Hexyldecyl Stearate | — | 16.0 | — | 16.0 | — | 16.0 | — | 16.0 |
| Cetiol OE | Dicaprylyl Ether | — | — | — | — | — | — | — | — |
| Cetiol CC | Dicaprylyl Carbonat | — | — | — | — | — | — | — | — |
| Eutanol G | Octyldodecanol | — | — | — | — | — | — | — | — |
| DC 245 | Cyclomethicone | — | — | — | — | — | — | — | — |
| Hydagen CAT | Triethylcitrate | — | — | — | — | — | — | — | — |
| Triclosan | Triclosan | — | — | — | — | — | — | — | — |
| Locron L | Aluminum Chlorohydrate | 40.0 | 40.0 | 40.0 | 40.0 | 40.0 | 40.0 | 40.0 | 40.0 |
| Rezal 36 GC | Aluminum Zirconium Chlorohydrate | — | — | — | — | — | — | — | — |
| Glycerol | Glycerine | 3.0 | 3.0 | 3.0 | 3.0 | 3.0 | 3.0 | 3.0 | 3.0 |

TABLE 1-continued

Antiperspirant creams and roll-ons

| Constituents | INCI | | | | | | | | |
|---|---|---|---|---|---|---|---|---|---|
| Hydagen DCMF | Chitosan | — | — | — | — | — | — | — | — |
| Water | Aqua | to 100 | to 100 | to 100 | to 100 | to 100 | to 100 | to 100 | to 100 |
| Preservation | | qs | qs | qs | qs | qs | qs | qs | qs |
| Viscosity | [mPas] | 15.000 | 20.000 | 7.000 | 9.000 | 1.000 | 1.000 | 15.000 | 12.000 |
| Structure | | +1 | +1 | +1 | +1 | 0 | 0 | +1 | +1 |
| Viscostability | | +1 | +1 | −1 | −1 | −2 | −2 | −1 | −1 |
| Stability | | +1 | +1 | −2 | −2 | −2 | −2 | −1 | −1 |
| Sensory impression | | +1 | +1 | +1 | +1 | — | — | — | — |

| Constituents | INCI | E1 | E2 | E3 | E4 | E5 |
|---|---|---|---|---|---|---|
| Eumulgin B2 | Ceteareth-20 | 2.0 | 2.0 | 2.0 | 2.0 | 1.0 |
| Eumulgin B3 | Ceteareth-30 | — | — | — | — | 1.0 |
| Eumulgin S2 | Steareth-2 | — | — | — | — | 1.0 |
| Lanette O | Cetearyl Alcohol | — | — | 1.0 | — | — |
| Lanette 22 | Behenyl Alcohol | — | — | — | — | — |
| Cutina MD | Glycerylstearate | — | — | — | 1.0 | — |
| C16/18-Monoglycerol ether | | | | | | |
| Glycerol ether mixture, Comp. Ex. 1, mono/di (1:4) | | | | | | |
| Glycerol ether mixture, Ex. 1, mono/di (1:1) | | 5.0 | 5.0 | 4.0 | 4.0 | 2.5 |
| Cetiol S | Diethylhexylcyclohexane | 16.0 | — | 2.0 | 2.0 | 8.0 |
| Eutanol G16S | Hexyldecyl Stearate | — | 16.0 | 2.0 | 2.0 | 2.0 |
| Cetiol OE | Dicaprylyl Ether | — | — | 4.0 | 4.0 | — |
| Cetiol CC | Dicaprylyl Carbonat | — | — | 4.0 | 4.0 | 2.0 |
| Eutanol G | Octyldodecanol | — | — | 2.0 | 2.0 | — |
| DC 245 | Cyclomethicone | — | — | 2.0 | 2.0 | 2.0 |
| Hydagen CAT | Triethylcitrate | — | — | — | — | 1.0 |
| Triclosan | Triclosan | — | — | — | — | 0.1 |
| Locron L | Aluminum Chlorohydrate | 40.0 | 40.0 | 40.0 | 40.0 | — |
| Rezal 36 GC | Aluminum Zirconium Chlorohydrate | — | — | — | — | 40.0 |
| Glycerol | Glycerine | 3.0 | 3.0 | 3.0 | 3.0 | 3.0 |
| Hydagen DCMF | Chitosan | — | — | — | — | 0.05 |
| Water | Aqua | to 100 | to 100 | to 100 | to 100 | to 100 |
| Preservation | | qs | qs | qs | qs | qs |
| Viscosity | [mPas] | 40.000 | 40.000 | 35.000 | 35.000 | 5.000 |
| Structure | | +2 | +2 | +2 | +2 | +2 |
| Viscostability | | +2 | +2 | +2 | +2 | +2 |
| Stability | | +2 | +2 | +2 | +2 | +2 |
| Sensory impression | | +2 | +2 | +2 | +2 | +2 |

TABLE 2

Skin-care creams

| Constituents | INCI | C9 | C10 | C11 | C12 | E7 |
|---|---|---|---|---|---|---|
| Emulgade PL 68/50 | Cetearyl Glucoside, Cetearyl Alcohol | 2.7 | 2.7 | 2.7 | 2.7 | 2.7 |
| Lanette O | Cetearyl Alcohol | 1.6 | — | — | — | — |
| Cutina MD | Glycerylstearate | — | 1.6 | — | — | — |
| C16/18 Monoglycerol ether | | — | — | 1.6 | — | — |
| Glycerol ether mixture, Comp. Ex. 1, mono/di (1:4) | | — | — | — | 1.6 | — |
| Glycerol ether mixture, Ex. 1, mono/di (1:1) | | — | — | — | — | 1.6 |
| Myritol 331 | Cocoglycerides | 4.0 | 4.0 | 4.0 | 4.0 | 4.0 |
| Cetiol OE | Dicaprylyl Ether | 2.0 | 2.0 | 2.0 | 2.0 | 2.0 |
| Cetiol V | Decyl Oleate | 2.0 | 2.0 | 2.0 | 2.0 | 2.0 |
| Dimethicone DC 200 | Dimethicone | 0.5 | 0.5 | 0.5 | 0.5 | 0.5 |
| Cetiol J600 | Oleyl Erucate | 3.0 | 3.0 | 3.0 | 3.0 | 3.0 |
| Glycerol | Glycerine | 3.0 | 3.0 | 3.0 | 3.0 | 3.0 |
| Water | Aqua | to 100 | to 100 | to 100 | to 100 | to 100 |
| Preservation | | qs | qs | qs | qs | qs |
| Viscosity [mPas] | | 50.000 | 60.000 | <5.000 | <10.000 | 140.000 |
| Structure | | +1 | +1 | +1 | +1 | +2 |
| Viscostability | | −2 | −1 | −2 | −2 | +2 |
| Stability | | +1 | +1 | −2 | −2 | +2 |
| Sensory impression | | +1 | 0 | — | — | +2 |

TABLE 3

Lipstick

| Constituents | INCI | E 8 |
|---|---|---|
| Myritol 318 | Caprylic/Capric Triglyceride | 14.0 |
| Myritol PC | Propylene Glycol Dicaprylate/Dicaprate | 6.0 |
| Eutanol G | Octyldodecanol | 17.0 |
| Beeswax 8100 (Carl&Co) | Cera Alba | 5.0 |
| Candelilla Wax | Candelina cera | 5.0 |
| Carnauba Wax | Carnauba cera | 7.0 |
| Monomuls 90 L 12 | Glyceryl Laurate | 3.0 |
| Dehymuls PGPH | Polyglyceryl 2 Dipolyhydroxystearate | 4.0 |
| Glycerol ether mixture, Ex. 1 | | 8.0 |
| Castor Oil | Hydrogenated Castor Oil | 10.0 |
| Copherol F 1300 | Tocopherol | 2.0 |
| Hydagen CMF | Chitosan Glycolate | 10.0 |
| Pigments | | as required |

TABLE 4

Sun creams and body and face care creams

| Constituents | INCI | E9 | E10 | E11 | E12 | E13 | E14 |
|---|---|---|---|---|---|---|---|
| Emulgade PL 6850 | Cetearyl Glucoside, Cetearyl Alcohol | 4.5 | — | — | — | — | 5.0 |
| Amphisol K | Potassium Cetyl Phosphate | 1.0 | — | — | — | — | 0.5 |
| Cutina GMS | Glyceryl Stearate | — | — | — | — | — | 0.5 |
| Lanette O | Cetearyl Alcohol | — | — | — | — | 2.5 | — |
| Glycerol ether mixture, Ex. 1 | | 1.0 | 1.0 | 1.5 | 3.0 | 3.0 | 3.0 |
| Eumulgin VL 75 | Lauryl Glucoside, Polyglyceryl-2 Dipolyhydroxystearate, Glycerin | — | 4.0 | 4.0 | — | 4.0 | — |
| Lanette E | Sodium Cetearyl Sulfate | — | 1.0 | 1.0 | — | — | — |
| Emulgade SE-PF | Glyceryl Stearate, Ceteareth-20, Ceteareth-12, Cetearyl Alcohol, Cetyl Palmitate | — | — | — | 5.0 | — | — |
| Eumulgin B1 | Ceteareth-12 | — | — | — | 1.0 | — | — |
| Dimethicone DC 200 | Dimethicone | — | — | — | 0.5 | 0.5 | 0.5 |
| Cetiol OE | Dicaprylyl Ether | 2.0 | — | — | 2.0 | — | — |
| Cetiol CC | Dicaprylyl Carbonate | — | — | 12.0 | — | 4.0 | 5.0 |
| Cetiol J600 | Oleyl Erucate | — | — | — | — | 2.0 | — |
| Cetiol S | Diethylhexylcyclohexane | — | — | — | 1.0 | — | — |
| Myritol 331 | Cocoglycerides | 8.0 | 12.0 | 10.0 | — | 2.0 | — |
| Cetiol B | Dibutyl Adipate | — | 10.0 | — | — | — | — |
| Cetiol 868 | Ethylhexyl Stearate | — | — | — | — | — | 4.0 |
| Eutanol G16 | Hexyldecanol | 3.0 | — | — | — | — | — |
| Copherol 1300 | Tocopherol | 1.0 | — | — | — | 1.0 | 1.0 |
| Cetiol SN | Cetearyl Isononanoate | — | — | — | 2.0 | — | — |
| Cegesoft PFO | Passionflora Incarnata (EU), Passiflora Incarnata Seed Oil (non EU) | — | — | — | — | — | 2.0 |
| Cegesoft PS6 | Olus (EU), Vegetable Oil (non EU) | — | — | — | — | — | 3.0 |
| Dow Corning 200 Fluid | Dimethicone | — | — | — | 2.0 | 0.5 | — |
| Neo Heliopan, Type 303 | Octocrylene | 7.0 | 9.0 | 9.0 | — | — | — |
| Neo Heliopan, Type 357 | Butyl Methoxydibenzoylmethane | — | — | — | 1.2 | — | — |
| Neo Heliopan, Type MBC | 4-Methylbenzylidene Camphor | 3.0 | — | — | 1.0 | — | — |
| Neo Heliopan AV | Ethylhexyl Methoxycinnamate | — | 7.5 | 7.5 | 3.0 | — | — |
| Zinck oxide NDM | Zinc Oxide | 7.0 | 5.0 | — | — | — | — |
| Eusolex T 2000 | Titanium Dioxide, Alumina, Simethicone | — | — | 5.0 | — | — | — |
| Veegum Ultra | Magnesium Aluminium Silicates | 1.5 | 1.5 | 1.5 | — | — | — |
| Keltrol T | Xanthan Gum | 0.5 | 0.5 | 0.5 | — | — | — |
| Hispagel 200 | Glycerin, Glyceryl Polyacrylate | — | — | — | 5.0 | — | — |
| Carbopol 980 (2%) | Polyacrylate | — | — | — | — | 15.0 | — |
| SFE 839 (GE Bayer Silicones) | Cyclopentasiloxane, Dimethicone/Vinyldimethicone Crosspolymer | — | — | — | — | 5.0 | — |
| Sepigel 305 (Seppic) | Polyacrylamide, C13-14 Isoparaffine, Laureth-7 | — | — | — | 1.0 | — | — |
| Dry Flo Plus (Starch and Chemical Limited) | Aluminium Starch Octenylsuccinate | — | — | — | — | 5.0 | — |
| Hydagen B | Bisabolol | — | 0.05 | 0.5 | — | — | — |
| 1,3 Butylene Glycol | Butylene Glycol | — | — | — | — | — | 2.0 |
| Glycerol | Glycerine | 3.0 | 3.0 | 3.0 | — | 2.0 | 2.0 |
| KOH (20% ig) | Potassium Hydroxide | — | — | — | — | 0.5 | — |
| Water, preservative | | to 100 | to 100 | to 100 | to 100 | to 100 | to 100 |

TABLE 5

Antiperspirant sticks and soft solids

| Constituents | INCI | C13 | C14 | C15 | E15 | E16 | E17 | E18 |
|---|---|---|---|---|---|---|---|---|
| Lanette 18 | Stearyl Alcohol | 20.0 | 16.0 | — | — | — | 4.0 | — |
| Cutina HR | Hydrogenated Castor Oil | — | 4.0 | — | — | 4.0 | 2.0 | — |
| | 12-Hydroxystearic Acid | — | — | 12.0 | — | — | — | 8.0 |
| | GP1 | — | — | — | — | — | — | — |

TABLE 5-continued

Antiperspirant sticks and soft solids

| Constituents | INCI | C13 | C14 | C15 | E15 | E16 | E17 | E18 |
|---|---|---|---|---|---|---|---|---|
| Glycerol ether mixture, Example 1 | | — | — | — | 20.0 | 16.0 | 8.0 | 4.0 |
| DC 245 | Cyclomethicone | 33.0 | 33.0 | 37.0 | 33.0 | 33.0 | 35.0 | 37.0 |
| Cetiol OE | Dicaprylyl Ether | 9.0 | 9.0 | 10.0 | 9.0 | 9.0 | 10.0 | 10.0 |
| Cetiol S | Diethylhexylcyclohexane | 15.0 | 10.0 | 18.0 | 10.0 | 15.0 | 18.0 | 18.0 |
| Arlamol E | PPG15 Stearyether | | 2.5 | | 2.5 | | | |
| DC 200 | Dimethicone | | 2.5 | | 2.5 | | | |
| Rezal 36 GP | Aluminum Zirconium Tetrachlorohydrex GLY | 23.0 | 23.0 | 23.0 | — | — | 23.0 | — |
| Locron P | Aluminum Chlorohydrate | — | — | — | 23.0 | 23.0 | — | 23.0 |
| Hardness (Penetration) | | 4.2 | 4.2 | 4.6 | 5.0 | 5.0 | 9.0 | 4.0 |
| Structure | | 0 | 0 | +1 | +1 | +1 | +2 | +2 |
| Stability | | −1 | +2 | +1 | +2 | +2 | +2 | +2 |
| Oil secretion | | −1 | +1 | +1 | +1 | +1 | +1 | +1 |
| Sensory impression | | +1 | +1 | +1 | +2 | +2 | +2 | +2 |

What is claimed is:

1. A glycerol ether mixture comprising
   a) at least one $C_{12-22}$ glycerol monoalkyl ether,
   b) at least one $C_{12-22}$ glycerol dialkylether,
   c) optionally, one or more $C_{12-22}$ glycerol trialkyl ether and
   d) optionally, one or more $C_{12-22}$ fatty alcohol,
   wherein components a) and b) together make up at least 50% by weight of the glycerol ether mixture and the ratio by weight of component a) to component b) is in the range from 3:1 to 1:2, and wherein components a) to d) make up at least 90% of the mixture, based on the weight of the mixture.

2. The glycerol ether mixture according to claim 1, wherein the ratio by weight of component a) to component b) is in the range from 1:1 to 1.3:1.

3. The glycerol ether mixture according to claim 1, wherein $C_{12-22}$ alkyl means a saturated or unsaturated, branched or unbranched alkyl group.

4. The glycerol ether mixture according to claim 1, wherein $C_{12-22}$ alkyl means a saturated and unbranched, alkyl group containing 16 to 18 carbon atoms.

5. The glycerol ether mixture according to claim 1, wherein $C_{12-22}$ alkyl is the same for all components a) to d), to the extent that components c) and d) are present.

6. The glycerol mixture according to claim 5, wherein $C_{12-22}$ alkyl means a saturated and unbranched alkyl group containing 16 to 18 carbon atoms.

7. The glycerol ether mixture according to claim 1, comprising
   35 to 45% by weight of component a),
   25 to 45% by weight of component b),
   1 to 5% by weight of component c) and
   8 to 27% by weight of component d).

8. A glycerol ether mixture comprising
   a) 40% by weight of at least one $C_{12-22}$ glycerol monoalkyl ether;
   b) 30 to 40% by weight of at least one $C_{12-22}$ glycerol dialkylether;
   c) 2 to 3% by weight of one or more $C_{12-22}$ glycerol trialkyl ether; and
   d) 13 to 22% by weight of one or more $C_{12-22}$ fatty alcohol;
   wherein components a) and b) together make up at least 50% by weight of the glycerol ether mixture and the ratio by weight of component a) to component b) is in the range from 3:1 to 1:2, wherein components a) to d) make up at least 90% of the mixture, based on the weight of the mixture, and wherein $C_{12-22}$ alkyl means a saturated and unbranched alkyl group containing 16 to 18 carbon atoms.

9. The glycerol ether mixture according to claim 1, wherein components a) to d) comprise at least 95% of the mixture, based on the weight of the glycerol ether mixture.

* * * * *